(12) United States Patent
Suranyi et al.

(10) Patent No.: US 11,344,030 B2
(45) Date of Patent: *May 31, 2022

(54) **MIXTURES OF SABADILLA ALKALOIDS AND *BACILLUS THURINGIENSIS* AND USES THEREOF**

(71) Applicant: McLaughlin Gormley King Company, Golden Valley, MN (US)

(72) Inventors: Robert A. Suranyi, Minneapolis, MN (US); Donald L. Sundquist, Minneapolis, MN (US)

(73) Assignee: McLaughlin Gormley King Company, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/582,427

(22) Filed: Sep. 25, 2019

(65) Prior Publication Data

US 2020/0015483 A1     Jan. 16, 2020

Related U.S. Application Data

(63) Continuation of application No. 15/637,399, filed on Jun. 29, 2017, now Pat. No. 10,426,172.

(60) Provisional application No. 62/357,899, filed on Jul. 1, 2016.

(51) Int. Cl.
| | |
|---|---|
| *A01N 63/23* | (2020.01) |
| *A01M 1/20* | (2006.01) |
| *A01N 25/00* | (2006.01) |
| *A61K 38/04* | (2006.01) |
| *C12N 1/20* | (2006.01) |
| *A61K 38/00* | (2006.01) |
| *C12N 1/00* | (2006.01) |

(52) U.S. Cl.
CPC ............... *A01N 63/23* (2020.01); *A01M 1/20* (2013.01); *A01N 25/006* (2013.01); *A61K 38/04* (2013.01); *C12N 1/20* (2013.01); *A01N 25/00* (2013.01); *A61K 38/00* (2013.01); *C12N 1/00* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 10,426,172 | B2 * | 10/2019 | Suranyi | A01N 25/006 |
| 2011/0033436 | A1 * | 2/2011 | Chen | A01N 63/30 |
| | | | | 424/93.461 |

FOREIGN PATENT DOCUMENTS

DE          25 52 295       * 5/1976

OTHER PUBLICATIONS

Ikawa et al. "The principal alkaloids of Sabadilla seed and their toxicity to Musca domestica". J Biol Chem. 1945, 159:517-524.*

* cited by examiner

*Primary Examiner* — Vera Afremova
(74) *Attorney, Agent, or Firm* — Wood, Phillips, Katz, Clark & Mortimer

(57) ABSTRACT

The present invention is directed to pesticidal mixtures comprising sabadilla alkaloids and *Bacillus thuringiensis* and methods of controlling pests including insects and mites by application of pesticidal mixtures comprising sabadilla alkaloids and *Bacillus thuringiensis*.

4 Claims, No Drawings

MIXTURES OF SABADILLA ALKALOIDS AND *BACILLUS THURINGIENSIS* AND USES THEREOF

FIELD OF THE INVENTION

The present invention is directed to pesticidal mixtures comprising sabadilla alkaloids and *Bacillus thuringiensis* and methods of controlling pests including insects and mites by application of pesticidal mixtures comprising sabadilla alkaloids and *Bacillus thuringiensis*.

BACKGROUND OF THE INVENTION

Arthropod pests are one of the major threats to human welfare and exert continued stress on the food supply and transmit a broad array of medical and veterinary diseases. Synthetic insecticides played a significant role and in many ways ushered in modern agriculture and pest control. However, the widespread use of synthetic insecticides also created numerous environmental challenges. The acute effects of synthetic pesticides on professional applicators and other end users are well-known but the chronic long term human health effects can be equally serious. Further, the use of synthetic insecticides has led to the development of resistant insect populations. Insecticide resistance is a complex phenomenon underlined by a diverse array of physiological mechanisms. Major mechanisms that are responsible for the development of insecticide resistance are metabolic detoxification, target site mutation, reduced cuticular penetration and behavioral avoidance.

Integrated Pest Management ("IPM") is a holistic approach to pest management. A fundamental aspect of insecticide utilization under the broader framework of IPM is the management of insecticide resistance (IRM) by the utilization of insecticide combinations that reduce the rate of resistance development. A combination of insecticides with different modes of action is fundamentally a concept based upon the idea of redundant killing of target insects. Insects adapted to one of the active ingredient in the combination product will still be killed by the other active ingredient. Mixtures can also reduce the amount of pesticides applied in the environment and the environmental impact associated with pesticide applications.

Most botanical insecticides are readily biodegradable and significantly less harmful to the environment and users than synthetic insecticides. The very short environmental persistence, usually less than 24 hours, of plant derived insecticides is favorable to the survival of non-target, beneficial parasites and predators which are important components of IPM. Unlike conventional insecticides which are typically based on a single active ingredient, plant derived insecticides usually comprise an array of chemical compounds that affect both behavioral and physiological functions of the target arthropods. The probability of pest resistance developing to plant derived insecticides is less than that for synthetic pesticides because these mixtures may have a variety of modes of action.

One effective naturally derived pesticide is found in the tissues of many of the plants of the genus *Schoenocaulon*, commonly referred to as sabadilla. The species with the longest history of use, and the most readily available, is *Schoenocaulon officinale*. The plant is indigenous to Central and South America and its seeds have been used for centuries for their insecticidal properties. The seeds contain several alkaloids including veratridine and cevadine, both of which are known to be active against arthropods.

*Bacillus thuringiensis* is a natural soil bacterium. Many *Bacillus thuringiensis* strains produce crystal proteins during sporulation called δ-endotoxins which can be used as biological insecticides. *Bacillus thuringiensis* produces crystals which paralyze the digestive system of some larvae within minutes. The larvae eventually die of starvation. One advantage of using *Bacillus thuringiensis* is that they are target specific. They do not harm humans or other non-target species. Yet another advantage of *Bacillus thuringiensis* is that they can be used on organic crops. Further, with no mandated pre-harvest interval, it can also be used on crops right before harvest.

*Bacillus thuringiensis* subsp. *aizawai* is commercially available as XenTari® (available from Valent BioSciences Corporation, XenTari is a registered trademark of Valent BioSciences Corporation). *Bacillus thuringiensis* subsp. *kurstaki* is commercially available as Dipel® (available from Valent BioSciences Corporation, Dipel is a registered trademark of Valent BioSciences Corporation). *Bacillus thuringiensis* subsp. *thuringiensis* is commercially available as Novodor (available from Valent BioSciences Corporation).

Thus, there is a need in the art for pesticide combinations that contain naturally derived pesticides that decrease health concerns to humans and also decrease the risk of the development of pesticide resistance.

SUMMARY OF THE INVENTION

In one aspect, the present invention is directed to pesticidal mixtures of sabadilla alkaloids and *Bacillus thuringiensis*.

In another aspect, the present invention is directed to methods of controlling pests, including insects and mites, comprising applying an effective amount of a mixture of sabadilla alkaloids and *B. thuringiensis*.

In a preferred aspect, the sabadilla alkaloids are derived from *Schoenocaulon officinale*.

DETAILED DESCRIPTION OF THE INVENTION

Applicant unexpectedly discovered that pesticidal mixtures of sabdilla alkaloids and *Bacillus thuringiensis* provided enhanced pesticidal activity compared to either pesticide alone. Specifically, this combination results in a reduced rate of resistance development. Further, Applicant discovered that pesticidal mixtures of sabadilla alkaloids and *Bacillus thuringiensis* were capable of controlling a large variety of arthropods.

The present invention is directed to pesticidal mixtures comprising an effective amount of sabadilla alkaloids and *B. thuringiensis*.

Sabadilla alkaloids may be derived from any species of *Schoenocaulon*. The genus *Schoenocaulon* includes the following species: *S. calcicola*, *S. caricifolium*, *S. comatum*, *S. conzattii*, *S. dubium* (alt. *S. gracile*), *S. framei*, *S. ghiesbreghtii* (alt. *S. drummondii*, *S. yucatanense*), *S. ignigenum*, *S. intermedium*, *S. jaliscense*, *S. macrocarpum* (alt. *S. lauricola*), *S. madidorum*, *S. megarrhizum*, *S. mortonii*, *S. oaxacense*, *S. obtusum*, *S. officinale*, *S. pellucidum*, *S. plumosum*, *S. pringlei*, *S. rzedowskii*, *S. tenorioi*, *S. tenue*, *S. tenuifolium*, *S. texanum*, and *S. tigrense*. In a preferred embodiment the *Schoenocaulon* sp. alkaloids are derived from *S. officinale*. In another preferred embodiment the *Schoenocaulon* sp. alkaloids are veratridine and cevadine.

*B. thuringiensis* includes many subspecies, each of which are suitable for use in the present invention alone, or in combination. Subspecies of *B. thuringiensis* include, but are not limited to, *aizawai, alesti, berliner, βnitimus, cameroun, canadiensis, colmeri, coreanensis, dakota, darmstadiensis, dendrolimus, entomocidus, fukuokaensis, galleriae, higo, indiana, israelensis, japonensis, japonensis Buibui, jegathesan, kenyae, kumamotoensis, kunthala, kurstaki, kyushuensis, Medellin, mexcanensis, morrisoni, neoleonensis, nigeriae, oloke, ongbei, ostriniae, pakistani, pondicheriensis, roskildiensis, san diego, shandogiensis, shanghai, silo, sotto, subtoxicus, tenebrionis, thompsoni, thuringiensis, tochigiensis, tohokuensis, tolworthi, toumanoffi, wuhanensis, yunnanensis*. In a preferred embodiment, *B. thuringiensis* comprises bacteria of subspecies selected from *aizawai, israelensis, kurstaki, thuringiensis* and combinations thereof. In a more preferred embodiment, *B. thuringiensis* comprises bacteria of subspecies selected from *aizawai, kurstaki, thuringiensis* and combinations thereof. In another preferred embodiment, *B. thuringiensis* comprises bacteria from a combination of subspecies selected from the group consisting of: *aizawai and kurstaki; aizawai and thuringiensis*; and *kurstaki and thuringiensis*.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will control the target pest. The "effective amount" will vary depending on the mixture concentration, the type of pest(s) being treated, the severity of the pest infestation, the result desired, and the life stage of the pest during treatment, among other factors. Thus, it is not always possible to specify an exact "effective amount." However, an appropriate "effective amount" in any individual case may be determined by one of ordinary skill in the art.

In a preferred embodiment, the ratio of sabadilla alkaloids to *B. thuringiensis* is from about 2:1 to about 1:200, preferably from about 1:1 to about 1:100.

In another preferred embodiment, the pesticidal mixtures of the present invention may contain one or more excipients selected from the group consisting of solvents, anti-caking agents, stabilizers, defoamers, slip agents, humectants, dispersants, wetting agents, thickening agents, emulsifiers, penetrants, adjuvants, synergists, polymers, propellants and/or preservatives.

The present invention is further directed to methods of controlling a pest comprising applying a pesticidal mixture comprising an effective amount of sabadilla alkaloids and *B. thuringiensis* to the pest or the pest's environment.

In a preferred embodiment, the pest is selected from an insect and a mite.

In an embodiment, the pest controlled is selected from the group consisting of aphids (Homoptera), whiteflies (Hemiptera), thrips (Thysanoptera), bed bugs (Hemiptera), fleas (Siphonaptera), caterpillars/worms (Lepidoptera), beetles (Coleoptera), cockroaches (Blattodea), flies (Diptera), ants (Hymenoptera), mosquitoes (Culicidae) and mites (Acari). In a preferred embodiment, the pest controlled are selected from the group consisting of common bed bugs (*Cimex lectularius*), green peach aphids (*Myzus persicae*), house fly (*Musca domestica*), yellow fever mosquito (*Aedes aegypti*), southern house mosquito (*Culex quinquefasciatus*), African malaria mosquito (*Anopheles gambiae*), common malaria mosquito (*Anopheles quadrimaculatus*) and German cockroach (*Blattella germanica*).

The pesticidal mixtures of the present invention can be applied by any convenient means. Those skilled in the art are familiar with the modes of application including spraying, brushing, soaking, in-furrow treatments, granules, pressurized liquids (aerosols), fogging or side-dressing.

In a preferred embodiment, sabadilla alkaloids are applied to the pest or the pest's environment at a rate from about 1 to about 1,000 grams per hectare ("g/HA"), preferably from about 10 to about 700 g/HA and most preferably from about 22 to about 560 g/HA.

In a preferred embodiment, *B. thuringiensis* is applied to the pest or the pest's environment at a rate from about 1 to about 5,000 g/HA, more preferably from about 100 to about 3,000 g/HA and most preferably from about 560 to about 2,242 g/HA.

As used herein, "control" a pest or "controlling" pest(s) refers to killing, incapacitating, repelling, or otherwise decreasing the negative impact of the pest on plants or animals to a level that is desirable to the grower or animal.

As used herein, "pest's environment" refers to any area that the pest is present during any life stage. One environment likely to be treated by the methods of the present invention includes the plants that the pest is living on and the surrounding soil. The pest's environment may also include harvested plants, gardens, fields, greenhouses, or other buildings, and various indoor surfaces and structures, such as furniture including beds, and furnishings including books, clothing, etc.

The articles "a," "an" and "the" are intended to include the plural as well as the singular, unless the context clearly indicates otherwise. For example, the methods of the present invention are directed to controlling "pest" but this can include control of a multiple pests (such as a more than one insect or more than one insect species or more than one mite or more than one mite species).

The following examples are intended to illustrate the present invention and to teach one of ordinary skill in the art how to use the extracts of the invention. They are not intended to be limiting in any way.

EXAMPLES

Dipel® was used as the source of *B. thuringiensis* subspecies *kurstaki* ("Btk").

Xentari® was used as the source of *B. thuringiensis* subspecies *aiwazai* ("Bta").

Novodor was used as the source of *B. thuringiensis* subspecies *thuringiensis* ("Btt").

Example 1—Control of Caterpillars/worms (Lepidoptera) with *B. thuringiensis* Subspecies *aiwazai*

In this study, the response of caterpillars/worms (Lepidoptera) to application of a 1:25, 1:1, 1:100 and 1:4 ratio of sabadilla (*S. officinale*)alkaloids to Bta will be observed. Specifically, sabadilla alkaloids and Bta will be applied to the pest at the respective rates of: 1) 22 g/HA and 560 g/HA; 2) 560 g/HA and 560 g/HA; 3) 22 g/HA and 2242 g/HA; and 4) 560 g/HA and 2242 g/HA.

The results of the study are predicted to show enhanced activity including reduced rates of resistance.

Example 2—Control of Caterpillars/Worms
(Lepidoptera) with *B. thuringiensis* Subspecies
*kurstaki*

In this study, the response of caterpillars/worms (Lepidoptera) to application of a 1:25, 1:1, 1:100 and 1:4 ratio of sabadilla (*S. officinale*)alkaloids to Bta will be observed. Specifically, sabadilla alkaloids and Bta will be applied to the pest at the respective rates of: 1) 22 g/HA and 560 g/HA; 2) 560 g/HA and 560 g/HA; 3) 22 g/HA and 2242 g/HA; and 4) 560 g/HA and 2242 g/HA.

The results of the study are predicted to show enhanced activity including reduced rates of resistance.

Example 3—Control of Caterpillars/Worms
(Lepidoptera) with *B. thuringiensis* Subspecies
*thuringiensis*

In this study, the response of caterpillars/worms (Lepidoptera) to application of a 1:25, 1:1, 1:100 and 1:4 ratio of sabadilla (*S. officinale*)alkaloids to Bta will be observed. Specifically, sabadilla alkaloids and Bta will be applied to the pest at the respective rates of: 1) 22 g/HA and 560 g/HA; 2) 560 g/HA and 560 g/HA; 3) 22 g/HA and 2242 g/HA; and 4) 560 g/HA and 2242 g/HA.

The results of the study are predicted to show enhanced activity including reduced rates of resistance.

What is claimed is:

1. A pesticidal mixture comprising an effective amount of sabadilla alkaloids and *Bacillus thuringiensis* kurstaki, wherein the ratio of sabadilla alkaloids to *Bacillus thuringiensis* kurstaki is from about 2:1 to about 1:200.

2. The mixture of claim 1, wherein the sabadilla alkaloids are derived from *Schoenocaulon officinale*.

3. The mixture of claim 1, wherein the sabadilla alkaloids are veratridine and cevadine.

4. The mixture of claim 1 further comprising one or more excipients selected from the group consisting of solvents, anti-caking agents, stabilizers, defoamers, slip agents, humectants, dispersants, wetting agents, thickening agents, emulsifiers, penetrants, adjuvants, synergists, polymers, propellants and/or preservatives.

* * * * *